US00PP21841P2

(12) United States Plant Patent
Stemkens

(10) Patent No.: US PP21,841 P2
(45) Date of Patent: Apr. 5, 2011

(54) ***AUBRIETA* PLANT NAMED 'AUBNERE'**

(50) Latin Name: *Aubrieta hybrida*
Varietal Denomination: Aubnere

(75) Inventor: Henricus Godefridus Wilhelmus Stemkens, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/660,970

(22) Filed: Mar. 8, 2010

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Annette H Para
(74) *Attorney, Agent, or Firm* — S. Matthew Edwards

(57) ABSTRACT

A new *Aubrieta* plant named 'Aubnere' particularly distinguished by the large, vibrant purple-violet flower color, compact and mounded plant habit that is early flowering, and has a longer flowering period.

1 Drawing Sheet

Latin name of the genus and species of the plant claimed *Aubrieta hybrida.*

Varietal denomination: 'Aubnere'.

BACKGROUND OF THE NEW PLANT

The present invention comprises a new *Aubrieta* plant, botanically known as *Aubrieta hybrida,* and hereinafter referred to by the variety name 'Aubnere'.

'Aubnere' is a product of a planned breeding program. The new cultivar has large, vibrant purple-violet flower color, compact and mounded plant habit that is early flowering, and has a longer flowering period.

'Aubnere' originated from a sibling cross made in April 2004 in a controlled breeding environment in Enkhuizen, Netherlands. The female parent was the proprietary plant designated 'G1258-52', unpatented, with red flowers. 'G1258-52' is later to flower and has smaller flowers than 'Aubnere'.

The male parent of 'Aubnere' was an unpatented plant identified as 'G1258-51' with violet flowers. 'G1258-51' is earlier to flower and has smaller flowers than 'Aubnere'.

The seed was sown in September 2004 and 'Aubnere' was selected as one flowering plant within the progeny of the stated cross in March 2005 in a controlled environment in Enkhuizen, Netherlands.

The first act of asexual reproduction of 'Aubnere' was accomplished when vegetative cuttings were propagated from the initial selection in March 2005 in a controlled environment in Enkhuizen, Netherlands.

BRIEF SUMMARY OF INVENTION

Horticultural examination of plants grown from cuttings of the plant initiated in March 2005, and continuing thereafter, has demonstrated that the combination of characteristics as herein disclosed for 'Aubnere' are firmly fixed and are retained through successive generations of asexual reproduction.

'Aubnere' has not been observed under all possible environmental conditions. The phenotype may vary significantly with variations in environment such as temperature, light intensity and day length.

No Plant Breeder's Rights for this cultivar have been applied for. 'Aubnere' has not been made publicly available more than one year prior to the filing of this application.

The following traits have been repeatedly observed and are determined to be basic characteristics of the new variety. The combination of these characteristics distinguishes this *Aubrieta* as a new and distinct variety.

BRIEF DESCRIPTION OF THE PHOTOGRAPHS

The accompanying photographic drawing shows typical flower and foliage characteristics of 'Aubnere' with colors being as true as possible with an illustration of this type. The photographic drawing shows a flowering potted plant of the new variety, and a close-up of the flowers.

DETAILED BOTANICAL DESCRIPTION

The plant descriptions, measurements and aforementioned photographs were taken in Gilroy, Calif. USA, in a greenhouse under natural light in February 2010. These plants used for the photographs and descriptions were about 5 months old, and were grown in an outdoor hoop house.

Color references are made to The Royal Horticultural Society Colour Chart (R.H.S.) 2001.

TABLE 1

DIFFERENCES BETWEEN THE NEW VARIETY 'AUBNERE' AND A SIMILAR VARIETY

| | 'Aubnere' | 'Audelmag' (U.S. Plant Pat. No. 18,465) |
|---|---|---|
| Flowering response: | Earlier | Later |
| Foliage color: | Darker green | Lighter green |
| Flower color: | Purple-violet | Purple |

Plant:
*Form, growth and habit.*—Compact and tightly mounded, freely branching, freely flowering.
*Plant height.*—7-8 cm.
*Plant height (inflorescence included).*—9-10 cm.
*Plant width.*—20-22 cm.
*Garden performance and tolerance to weather.*—Very good.

Roots:
*Number of days to initiate roots.*—About 12 days at about 18 degrees C.
*Number of days to produce a rooted cutting.*—3-4 weeks at 18 degrees C.
*Type.*—Fine, fibrous, free branching.
*Color.*—RHS N155B but whiter.

Foliage:
*Arrangement.*—Alternate.
*Immature, leaf color, upper surface.*—RHS 137C but a little more yellow.
*Lower surface.*—RHS 144A.
*Mature, leaf color, upper surface.*—RHS 137C but a little more yellow.
*Lower surface.*—RHS 144A.
*Length.*—2.2-2.5 cm.
*Width.*—1.2-1.7 cm.
*Shape.*—Ovate to almost spathulate.
*Base shape.*—Attenuate.
*Apex shape.*—Mucronulate.
*Margin.*—Dentate.
*Texture, upper surface.*—Stellate hair.
*Lower surface.*—Stellate hairs.
*Color of veins, upper surface.*—RHS 144B.
*Color of veins, lower surface.*—RHS 144C but slightly darker.
*Venation pattern.*—Pinnate.
*Petiole color.*—RHS 144B.
*Length.*—1.0-1.2 cm.
*Diameter.*—0.4 cm.
*Texture.*—Stellate hairs on both sides.

Stem:
*Color of stem.*—RHS 144D to RHS 145D.
*Length of stem.*—0.8-0.9 cm.
*Diameter.*—0.2 cm.
*Length of internodes.*—0.4-1.0 cm.
*Texture.*—Stellate hairs and hirsute.
*Color of peduncle.*—RHS 144A to RHS 144B.
*Length of peduncle.*—0.4-0.5 cm.
*Peduncle diameter.*—0.1-0.15 cm.
*Texture.*—Stellate hairs and hirsute.

Inflorescence:
*Type.*—Single, cruciform, composed of 4 petals; flowers held above the plant.
*Quantity of inflorescences per plant.*—About 50.
*Quantity of inflorescences per lateral stem.*—1-5.
*Lastingness of individual blooms on the plant.*—About 1 week.
*Fragrance.*—None.

Bud: (just before opening/showing color)
*Color.*—RHS N81A.
*Length.*—0.9-1.1 cm.
*Width.*—0.3-0.4 cm.
*Shape.*—Oblong.

Corolla immature inflorescence:
*Diameter.*—1.5 cm.
*Color of petals, upper surface.*—RHS N80A with RHS N79C veining.
*Lower surface.*—RHS N80D.

Mature inflorescence:
*Flower diameter.*—2.0 cm.
*Depth.*—1.5 cm.
*Petal color, upper surface.*—RHS N80B, and a little darker at the outer margins, RHS N79C veining, and a 'eye' color of about RHS 1A with a slight suffusion of RHS 69D.
*Lower surface.*—RHS N80D but a little lighter.
*Length of petal.*—0.9-1.0 cm.
*Width of petal.*—0.8-0.9 cm.
*Shape.*—Spathulate.
*Apex shape.*—Rounded.
*Margin.*—Entire but somewhat wavy.
*Petal texture, upper surface.*—Papillose.
*Lower surface.*—Papillose.
*Corolla tube color inside.*—RHS 1B.
*Tube color outside.*—Closest to RHS 144B.
*Corolla texture, inside.*—Papillose.
*Outside.*—Papillose.

Calyx:
*Quantity.*—4.
*Color, upper surface.*—RHS 144B.
*Lower surface.*—RHS 144B.
*Length.*—0.5-0.7 cm.
*Width.*—0.1-0.2 cm.
*Shape.*—Oblong.
*Apex shape.*—Acute.
*Based.*—Fused.
*Margins.*—Entire.
*Texture, upper/inner surface.*—Smooth.
*Lower/outer surface.*—Stellate hairs.

Reproductive organs gynoecium:
*Pistil quantity.*—1.
*Length.*—0.7 cm.
*Style color.*—RHS 143B.
*Style length.*—0.4 cm.
*Stigma color.*—RHS 143A.
*Stigma shape.*—Not observed.
*Ovary color.*—Not observed.

Androecium:
*Stamens, quantity.*—6.
*Color of filaments.*—RHS 155B.
*Length filaments.*—1.1 cm.
*Anther color.*—RHS 18A.
*Anther length.*—0.1 cm.
*Anther shape.*—Ovate.
*Color of pollen.*—RHS 8B.
*Pollen amount.*—Normal.
*Fertility/seed set.*—Has not been observed.

Disease/pest resistance: Disease/pest resistance has not been observed.

What is claimed is:

1. A new and distinct variety of *Aubrieta* plant named 'Aubnere' substantially as illustrated and described herein.

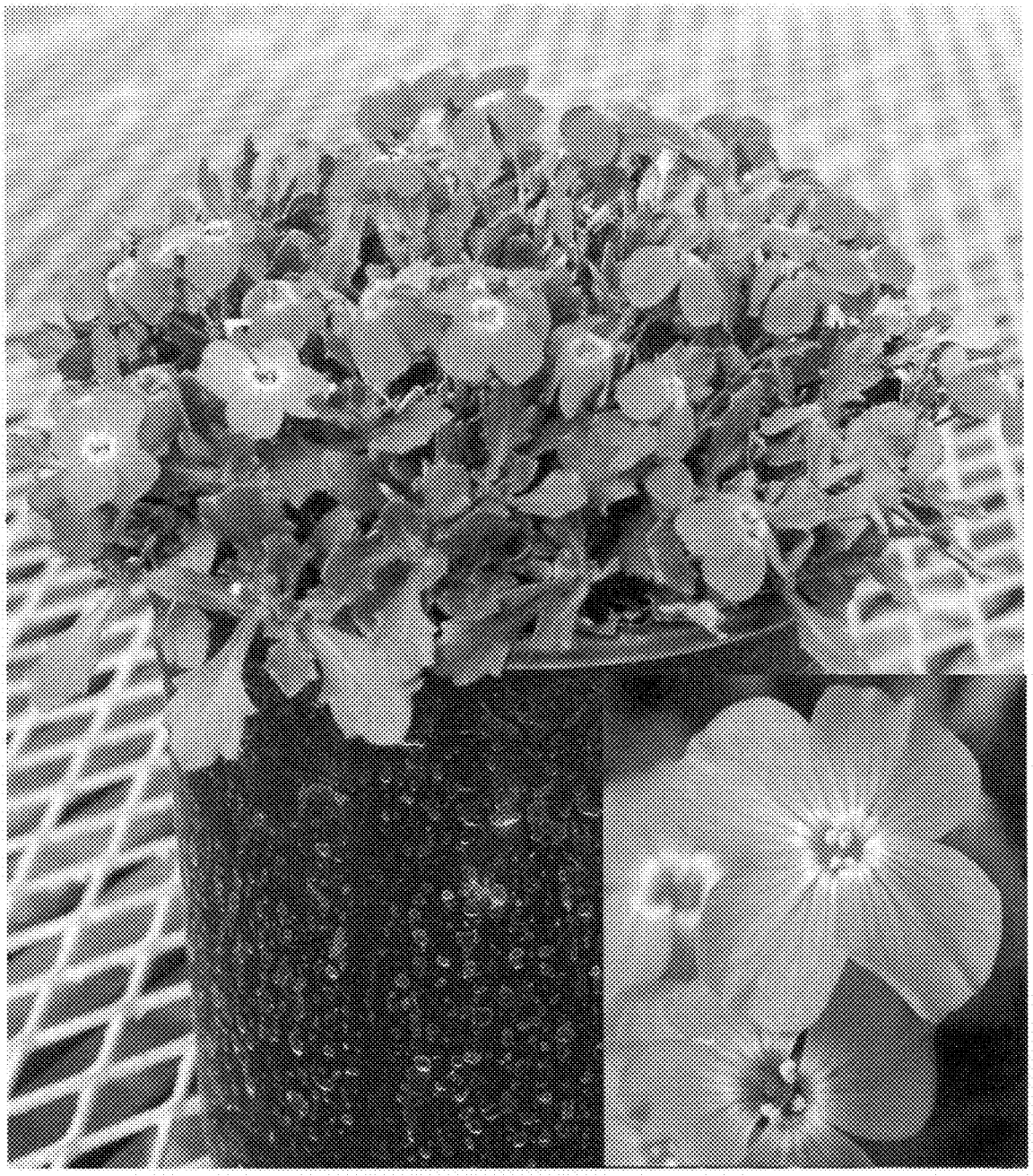

* * * * *